United States Patent [19]

Baker

[11] Patent Number: 4,808,447

[45] Date of Patent: Feb. 28, 1989

[54] PRESERVED FLOWERS AND OTHER SUBSTRATES

[76] Inventor: Marion A. Baker, 18161 Windsor Dr., Orange, Calif. 92667

[21] Appl. No.: 61,916

[22] Filed: Jun. 11, 1987

Related U.S. Application Data

[63] Continuation-in-part of Ser. No. 922,538, Oct. 23, 1986, abandoned.

[51] Int. Cl.$^4$ .............................................. A01N 3/00
[52] U.S. Cl. ......................................... 428/17; 427/4; 428/24
[58] Field of Search ............... 428/24, 17; 47/DIG. 2; 427/4

[56] References Cited

U.S. PATENT DOCUMENTS

| | | | |
|---|---|---|---|
| 2,606,843 | 8/1952 | Fessenden | 427/4 |
| 2,658,836 | 11/1953 | Fessenden | 427/4 |
| 4,205,059 | 5/1980 | Haggens | 427/4 |

FOREIGN PATENT DOCUMENTS

| | | | |
|---|---|---|---|
| 0141741 | 12/1978 | Japan | 427/4 |
| 0007601 | 2/1982 | Japan | 427/4 |
| 0073501 | 4/1984 | Japan | 427/4 |

*Primary Examiner*—Sam Silverberg
*Attorney, Agent, or Firm*—Joseph E. Mueth

[57] ABSTRACT

The process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, said substrate including naturally occurring active hydrogen compounds as part of its structure, exposing the substantially dried substrate to a cross-linking compound containing a plurality of groups which are complementary reactive with the said active hydrogen groups to form a high molecular weight three dimensional cross-linked polymeric network between the active hydrogen groups of said substrate and the compound containing said complementary reactive groups.

A process of dehydrating flower blooms, and other natural carbohydrate products such as flower stems, leaves and vegetables with good shape and color retention which comprises immersing such substrate in a water-miscible, organic solvent which forms a minimum boiling point azeotrope with water, and evaporating the solvent-water mixture in a controlled atmosphere that keeps the water vapor concentration leaving the substrate in the evaporating gas greater than it is in the liquid present.

16 Claims, No Drawings

PRESERVED FLOWERS AND OTHER SUBSTRATES

This application is a continuation-in-part of U.S. patent application Ser. No. 922,538, filed Oct. 23, 1986, now abandoned the disclosure of which is expressly incorporated herein by reference.

BACKGROUND OF THE INVENTION

In the part various procedures for the preservation of flowers and other naturally occurring materials of similar carbohydrate nature have been proposed. The basic problem is that the preservation process has usually adversely effected the appearance, shape and/or texture of the resultant treated substrate. These effects often reduced the value and esthetic appeal of the substrate.

The prior art known to applicant is as follows:

Waszkiewicz, Jr., U.S. Pat. No. 3,563,780 describes a process for preserving flowers in which a fresh flower is first dried by burying it in dry silica gel. The dried flower is then dipped in a solution of an ester-typed acrylic resin and a solvent, and air dried.

Yordan U.S. Pat. No. 3,607,488 discloses a process in which naturally occurring plant material is comminuted to a desired size and shape, e.g., one-sixteenth to one inch, treated with a preservative, e.g. aqueous "Formalin", dyed, dried and coated with a waterproof resinous sealer.

Mazzucato et al U.S. Pat. No. 3,645,766 describes a drying and storing method for flowers and leaves which are immersed in a heated powder material having a high absorbing power, so that dehydration process gradually occurs in the absence of light and active atmosphere gases, whereupon the dried flower is preheated to paraffin melting temperature and immersed for a few minutes in a melted paraffin or wax bath, then removed and cooled to room temperature.

Rovetti U.S. Pat. No. 3,861,053 described plant and related materials are dried in silica gel and borax, and the dried materials protected by coating with a solution of paraffin in an inert hydrocarbon solvent.

von Hagens U.S. Pat. Nos. 4,205,059, 4,244,992 and 4,278,701 provide a solid, substantially anhydrous body of animal or vegetal tissue and a synthetic resin substantially uniformly distributed in the tissue which is prepared from a water-bearing, normally soft tissue, normally subject to rapid decomposition and loss of weight by evaporation of its water content. The product is prepared by substantially completely removing the water content while substantially maintaining the original tissue shape and volume, uniformly impregnating the water-free tissue with a fluid precursor composition capable of being polymerized into a solid synthetic resin, and holding the impregnated tissue under polymerization conditions until the precursor composition is cured to a solid resin more rigid than the original tissue.

Fessenden U.S. Pat. No. 2,567,929 provides a process for preserving plant tissues comprising, immersing the tissues in a color stabilizing and preserving solution containing butyl alcohol, thiourea, boric acid, and ions of sodium, phosphate and borate, then allegedly dehydrating the tissues under conditions whereby their natural physical shape and stabilized color are retained, then impregnating the tissues with a solution containing hydrogenated rosin, and then applying to the impregnated tissues a coating of a vinyl chloride-acetate copolymer. This patent discloses that the butyl alcohol treatment can be carried out at 5° C. for around thirty minutes which is of inadequate duration to accomplish significant dehydration of a fully intact bloom (i. e. not just petals).

The Fessenden U.S. Pat. No. 2,606,843 discloses surrounding the impregnated and/or coated material by surrounding it with a relatively thich mass of transparent, moisture-excluding, durable plastic.

The U.S. Pat. No. 2,658,836 to Fessenden shows dehydration plus impregnation with a moisture-resistant shape reinforcing substance, some of which are polymers.

Romero-Sierra U.S. Pat. No. 4,248,734 relates to a solution and process for preserving Douglas Fir needles while preventing shedding thereof from the branch to which they are naturally attached, producing a natural looking product suitable for display purposes. The branches, with attached needles, are immersed in a solution comprising water, ethyl alcohol, ethylene glycol, propionic acid, glycerin, formalin, propylene glycol, citric acid, magnesium sulphate, cupric sulphate, sodium sulphite and seaweed extract, for a period of up to about two weeks and subsequently air dried.

Romero-Sierra U.S. Pat. No. 4,272,571 describes a process for preserving substantially any variety of flower while retaining the natural colors thereof, in which the flower is immersed in an essentially water-free composition comprising: at least one dehydrating alcohol, a carboxylic acid, a urea-containing compound, an alkaline citrate, and zero to an effective amount of at leat one of a silicone fluid, a silicone resin, an alkaline formaldehyde sulfozylate, alumuminum or magnesium sulphate and cupric or other transitional metal sulphate for sufficient time to dehydrate the flower, said composition also containing a sufficient quantity of a least one compound in the group consisting of an alkaline phosphate, a lower carboxylic acid and phenol so as to ensure that the composition has a pH in the range 5-7. Following immersion the flower is dried and coated with a silicone resin.

Romero-Sierra U.S. Pat. No. 4,278,715 described a process for preserving green colored plant tissues while retaining the natural green color thereof, in which the tissues are immersed in a solution comprising: water, at least one monohydric alcohol, at least one preservative component selected from the group comprising lower carboxylic acids, di and tri hydric alcohols, and sufficient buffering and mordant reagents to control the pH and osmolality of said solution, so as to permanently retain said green color in said tissues. In a preferred embodiment the treated tissue is subjected to a secondary treatment in a holding solution comprising glycerin and water.

Romero-Sierra U.S. Pat. No. 4,328,256 describes a process for preserving green colored plant tissues and in particular coniferous needles, holly and low fiber leaves such as mosses, lichens and ferns in which selected leaves are immersed in a solution comprising water, 2-propanol, propionic acid, sulphurous acid, formalin, formic acid, ethylene glycol, and optionally minor amounts of compouns selected from the group consisting of cupric sulphate, cupricchloride, 20-20-20 fertilizer, citric acid, DBE, magnesium sulphate, acetic acid, cupric acetate, cupric nitrate, sodium phosphate, sodium sulfite, butylated hydroxytolulene and glycerol, for a sufficient time to exchange the naturally occurring water in the tissues with the "chemical water" of the solution and thereby permanently retain and biologically fix the green color of the leaves.

Japanese Patent No. 0,007,601 (1982) provides for maintaining color of cut flower used in flower arrangements by dehydrating, and immersing in grape sugar solution. It is then treated with an acetone solution containing thioures and irradiated with a high frequency electric current. The flower is treated with a treating agent consisting of dissolbed nitrated cotton, acetone and a liquid polyester, and finally dried and ornamentally arranged.

Japanese Patent No. 0,010,033 (1979) discloses living flowers and leaves which are treated and dehydrated with a water-soluble organic solvent, and impregnated with polyethylene glycol. A main stem having flowers and leaves is immersed in a solution containing N,N-dimethylformamide and the solution is gradually heated to 60 degrees C. The main stem is taken out from the solution, rinsed with methanol and immdeiately immersed in a mixed solvent of 50 parts by weight of polyethylene glycol and 50 parts by weight of methanol for 10 hours. The methanol acts as a diluent for the glycol. The stem is taken out from the mixed solvent and air dried naturally at ambient temperature over ten days.

Japanese Patent No. 0,073,501 (1984) pertains to the outer surface of a living body (e.g. vegetable, such as leaves, flowers, etc., or insects, etc.) having cuticular layer which is dried and dipped in a solution of a urethane oligomer in a solvent (e.g. methylene chloride, etc.). The body so treated is dried and then coated with a polyester paint containing a peroxide as a curing catalyst. The polyester paint may be mixed with an acrylic dental adhesive. The urethane oligomer used includes ones to be used as concrete sealants.

The Pfitzer, U.S. Pat. No. 547,227 from 1895, shows dehydration of the plants with alcohols, ethers, aldehydes, ketones, and certain hydrocarbons. It calls for the plant parts to be either dried in the open air or in the presence of hydroscopic substances. This patent also speaks of coating with shellac.

Valentine U.S. Pat. No. 1,779,299 shows preliminary treatment with alcohol and coating with a varnish or emulsion and a final coating of gelatin. The patent also, discloses adding a final waterproofing solution, which is a solution of celluloid or rubber.

The Joffe U.S. Pat. No. 2,646,512 employs salicylic acid in isopropyl alcohol in various materials.

D. A. Johansen, Science, Vol. 82, pp. 253–4, (Sept. 13, 1935), discloses what is said to be the dehydration of various plant tissues by the use of dioxane and tertiary butyl alcohol.

The dehydration efforts using lower alkanols, according to the prior art, are ineffective because the high temperatures and/or inadequate immersion and preparation results in an unacceptably distorted and unstable Free Standing Product. This invention discloses more statisfactory methods of dehydrating vegetable matter.

In contrast to the prior art, the present invention provides a chemical linkage between the dehydrated substrate and the infiltration material. Thus, in the present invention, the interstitial spaces are not simply replaced, i.e. (cell walls surrounded by another) material. Rather, the basic composition of the substrate is extended or added to, forming a continuous structure having many beneficial characteristics.

The present inventions represent a substantial advance in the this art and it is to be expected that it will be widely adopted by those skilled in the art.

SUMMARY OF THE INVENTION

Briefly, this invention comprises preserved flower blooms and other natural predominantly carbohydrate products such as flower stems, leaves, and vegetables, sometimes hereinafter referred to simply as a substrate, being free standing and having a natural fresh appearance maintained over prolonged periods.

This invention further includes the process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, said substrate including naturally occurring active hydrogen compounds as part of its structure, exposing the substantially dried substrate to a crosslinking compound containing a plurality of groups which are complementary reactive with the said active hydrogen groups to form a high molecular weight three dimensional crosslinked polymeric network between the active hydrogen groups of said substrate and the compound containing said complementary reactive groups.

In another aspect, this invention includes, a process of dehydrating flower blooms, and other natural carbohydrate products such as flower stems, leaves and vegetables with good shape and color retention which comprises immersing such substrate in a water-miscible, organic solvent which forms a minimum boiling point azeotrope with water, and evaporating the solvent-water mixture in a controlled atmosphere that keeps the water vapor concentration leaving the substrate in the evaporating gas greater than it is in the liquid present.

It is an object of this invention to provide improved and more esthetically attractive preserved natural substrates.

It is an equally important object of this invention to provide novel process of providing such substrates.

The blooms and other substrates of this invention are flexible and durable, and are unaffected by normal variations of temperature, humidity and light. They are not permanently deformed by heat and pressure the way an uncrosslinked material would be, and they are not affected by casual exposure to liquid water.

No other preserved or artificial flowers possess all of these properties, nor do they appear to be "alive", as this product does.

These and other objects and advantages of this invention will be apparent from the detailed description which follows.

DESCRIPTION OF PREFERRED
EMBODIMENTS I. The following generally describe the carbohydrate substrates useful in the practice of this invention. Substrates contain active hydrogen atoms not including water, the water having been substantially removed by priod dehydration.

For example:
A. Flowers Blooms
B. Flower Stems and Leaves
C. Vegetable

It is is quite easy to preserve a great number of blossoms, blooms, and vegetable matter. Such things as Roses, Orchids, Bougainvillia, Gardenia and even Tulips have been successfully preserved according to this invention with remarkable fidelity. II. Functionally reactive compounds containing one or more active hydrogen groups can optionally be applied to substrates to infiltrate, include the familiar glycols, sorbitol, alkylene dithiols, hydroxy carboxylic acids, amides, and the like.

These compounds contain at least one and usually two or more, reactive hydrogen moieties i.e. R-OH, R(OH)$_2$, H$_2$NCO-R-OH, etc. and they may also contain other reactive moieties such as R=O, —C=C—, R-COOH, allyl, acetylenic, etc.

Particularly preferred compounds are:

A. Polymer acetals (Polyvinyl formal, polyvinyl butyral, etc.) containing some hydroxyl groups.

B. Polyols, that is, substances containing hydroxy groups such as:
   1. Polyether polyols such as poly tetra hydro furan, polyethylene/polypropylene glycols, and polythiols.
   2. Polester polyols such as polycaprolactones.
   3. Aliphatic polyamides, low mol weight nylons.
   4. Polyacrylate/methacrylate polyols.
   5. Polyolefin polyols.
   6. Alkyds contianing Hydroxyl groups.
   7. Sugars and modified sugars.
   8. Epoxies
   9. Low mol weight polyols such as butane diol trimethyol propane, and Sorbitol.

C. Compounds with differing active hydrogen groups in the same molecule such as lactic acid, hydroxyl ethyl acrylamide or dihydroxyethyl maleate.

The compound of II are not required, but can be used in one preferred embodiment of the invention. III. Substances that will react "in situ" with substances named in I and II (if present) in the essential absence of water to form a composite polymer network containing elements of I, II, (if present) and III.

These compounds contain a plurality of groups having complementary reactivity with substances named in I and II (if present) and include:

A. Aromatic and aliphatic isocyanates (TDI, MDI, HMDI, etc.) and prepolymer isocyanates and NCO terminated polymers, and certain NCO containing derivitives.

B. Polyfunctional aldehydes
   1. glyoxal
   2. glutaraldehyde
   3. acrolein

C. Functional resins suah as melamine, hexamethylol melamine, uerau-formaldehyde and phenol-formaldehyde. (most all aminoplasts).

D. Polyamide-epichlorohydrin resins.

E. Werner type complexes

F. Organic titanates

It is often preferred to use a non-yellowing polyurethane prepolymer to cross-link. One preferred cross-linker is methylene bis (4-cyclohexyl) diisocyanate. Since it is less reactive than its aromatic analog, additional dibutyl tin dilaurate catalyst is needed, as well as cure temperatures in the 130°-180° F. range.

Reaction involves I, II, (if present) and III simultaneously or serially to form a finished product.

Many methods of introducing substance II (if present) into substance I are contemplated such as: use of volatile ether solvents, volatile amide solvents, volatine ester solvent, volatile alcohol solvent, volatile ketone solvent, volatile hydrocarbon solvent, volatile chlorinated organic solvent, or mixtures or molecules containing more than one of the moieties mentioned above.

Also, substance II (if present) materials that are liquid can be introduced by immersing substance I materials in them.

The following examples are presented to illustrate the invention and is not limiting in any way.

EXAMPLE 1

A freshly cut rose bloom with a large hole drilled in the receptacle, is immersed in 80/20% by volume mixture of tertiary butyl alcohol and isopropyl alcohol at about 32° F. for 48 hours. The rose is then removed and dried in a dry nitrogen gas jet for a few minutes to remove excess alcohols. The rose is then dried under vacuum (100 mm Hg Pressure Absolute) for one hour. The rose is next immersed in a 10% solution of polyvinyl formal in diacetone alcohol. Then the rose is then placed in a high vacuum of 25 – 100 Hg for several hours after which is emerges in a substantially dry state impregnated with polyvinyl formal.

The rose is then immersed in a mixture of ethyl acetate containing 10% of an MDI prepolymer (equivalent weight of 242). The rose is then placed in a dry nitrogen atmosphere for 24 hours at 100° F. The product that emerged is quite reminiscent in shape, color, and appearance of the original rose and has not lost any form or shape after one year. The bloom is still tough and flexible.

When the foregoing is repeated using a high mol weight hydroxyl-terminated polyethylene/prophylene glycol and methylene bis(4-cyclohexyl) diisocyanate plus dibutyldilorate, similar results are obtained if bloom is heated to 160° F. in dry nitrogen atmosphere for several hours.

Several other variations on the foregoing are also within the scope of this invention. For example, acrylate and/or polycoporlactone, polyacrylic/methacrylic esters, polyethers that have more than one hydroxyl function may be used.

It has also been found that certain alcohol soluble resins such as shellac and/or polymers such as roisn, hydrogenated rosin and polyvinyl acetal can be beneficially added to the alcohol treating solution in order to increase the strength of the bond between the petal and the receptacle in later handling procedures. Of equal importance is the fact that all the flower parts are exceedingly brittle at this state and must be manipulated with extreme care. The resin and/or polymer increases the threshold of force that will cause damage in the handling procedures when the flower is removed from the dehydrating solution.

EXAMPLE 2

A fresh "Privet" rose bloom, with hole in the recepticle, was placed in a glass jar containing one quart of 99.8% isopropyl alcohol at a temperature of 32° F., in which had been dissolved 8 grams of 50% phosphoric acid and 5 grams of Irganox 245 antioxidant.

After being held for 2 days at 32° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:

20 parts—Tone polymer P-300 (a linear polyester diol from caprolactone, Mol. weight 11,000 Equivalent weight-5500, Union Carbide)
1 part—methylene diphenyldiisocyanate
trace—dibutyl tin dilaurate
79 parts—methyl ethyl ketone The bloom was then removed from the solution and placed in dry air and held at a temperature of 130° F. for 2 hours. The resultant product was quite flexible and tough, and life like in appearance and is unaffected by normal variations of temperature, humidity and light.

EXAMPLE 3

A fresh "Privet" rose bloom, with hole in the recepticle, was placed in a glass jar containing one quart of 99.8% isopropyl alcohol at a temperature of 40° F., in which had been dissolved 5 grams of Irganox 245 antioxidant.

After being held for 2 days at 40° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:

20 parts—Tone polymer P-300 (diol capped poly caprolactone Mol. wt. 11,600, Equivalent weight=5,500, Union Carbide)
1 part—methylene diphenyldiisocyanate
trace—dibutyl tin dilaurate
79 parts—methyl ethyl ketone The bloom was then removed from the solution and placed in dry air and held at a temperature of 130° F. for 2 hours.

The resultant product was quite flexible and tough, and life like in appearance, but somewhat more purple than the original bloom. It is unaffected by normal variations of temperature, humidity and light. It also, is not permanently deformed by pressures that deform thermoplastic materials.

EXAMPLE 4

A fresh "Bacarra" rose bloom, with hole in the recepticle, was placed in a glass jar containing one quart of 99.8% isopropyl alcohol at a temperature of 32° F., in which had been dissolved 8 grams of 50% phosphoric acid.

After being held for 2 days at 32° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:

20 parts—Tone polymer P-300
2 parts—Resimene 970 (Urea-Formaldehyde resin Monsanto))
½ part—38% Sulfuric acid
78 parts—mixture of ethyl ketone 70%-isopropyl alcohol 30°

The bloom was then removed from the solution and placed in dry air and held at a temperature of 180° F. for 4 hours.

The resultant product was somewhat flexible and tough, and life like in appearance, and excellent clarity of color.

EXAMPLE 5

A fresh "Privet" rose bloom, with hole in the recepticle, was placed in a glass jar containing one quart of 99.8% isopropyl alcohol at a temperature of 40° F., in which had been dissolved 5 grams of Irganox 245 antioxidant.

After being held for 3 days at 40° F. in this sealed container, the bloom was removed, excess solvent was removed from it by briefly blowing dry nitrogen gas on it, and it was then quickly placed in a one gallon large mouth glass bottle, a lid with a small ½" hole was screwed on the bottle and the bottle was held at a temperature 120° F. for 24 hours.

After 24 hours the dried bloom was removed and dipped in a solution containing:

18 parts—Terathane 1000 (polyTHF diol))
2 parts—Tone polyol 301 (Triol low mol. weight based on Caprolactone)
7 parts—Methylene diphenyl diisocyanate
trace—dibutyl tin dilaurate
68 parts—methyl ethyl ketone The bloom was then removed from the solution and placed in dry air and held at a temperature of 130° F. for 2 hours.

The resultant product was flexible and tough, and life like in appearance, and excellent clarity of color.

EXAMPLE 6

A fresh "Privet" rose bloom, with hole in the recepticle, was placed in a glass jar containing one quart of 99.8% isopropyl alcohol at a temperature of 45° F., in which had been dissolved 8 grams of 50% phosphoric acid.

After being held for 1 day at 45° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:

20 parts—Terathane 1000=( a poly tetrahydrofuran diol-mol-weight, 980, Equivalent weight 490, du Pont)
5 parts—Resimene 970 (a fast curing UF resin monsanto)
3 parts—38% sulfuric acid
73 parts—(methyl ethyl ketone 70% -isoprypryl alcohol 30%)

The bloom was then removed from the solution and placed in dry air and held at a temperature of 180° F. for 4 hours The resultant product was rather frangible, but gave a glossy, wet appearance and bright color and is unaffected by normal variations of temperature, humidity and light.

EXAMPLE 7

A fresh "Privet" rose bloom, with hole in the recepticle, was placed in a glass jar containing one quart of 99.8% isopropyl alcohol at a temperature of 40° F., in which had been dissolved 8 grams of 50% phosphoric acid.

After being held for 2 days at 40° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:
- 20 parts—RJ-1000 Resious Polyol (A styrene-allyl alcohol copolymer. Mol weight 2340 equivalent weight 300)
- 10 parts—Resimene 970 (fast cure UF resin) Monsanto
- 3 parts—38% sulfuric acid
- 67 parts—(methyl ethyl ketone 70% isopropyl alcohol 30%)

The bloom was then removed from the solution and placed in dry air and held at a temperature of 180° F. for 2 hours.

The resultant product was rigid and frangible and is easily mistaken for porcelain. The color is brilliant and is unaffected by normal variations of temperature, humidity and light, in fact, it was unaffected when washed in an automatic dishwahes (no soap, no heat).

EXAMPLE 8

A fresh "Privet" rose bloom, with hole in the recepticle, was placed in a glass jar containing one quart of 99.8% isopropyl alcohol at a temperature of 40° F., in which had been dissolved 8 grams of 50% phosporic acid and 5 grams of Irganox 245 antioxidant.

After being held for 2 days at 40° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the openinng.

After 24 hours the dried bloom was removed and dipped in a solution containing:
- 20 parts—(Cargill) short oil now drying alkyl containing excess residual primary hydroxyls. Equivalent weight=Ca500, mol weight=not applicable
- 8 parts—Hydrogenated methylene diphenyldiisocyanate
- trace—dibutyl tin dilaurate
- 20 parts—Xylene
- 59 parts—methyl ethyl ketone The bloom was then removed from the solution and placed in dry air and held at a temperature of 160° F. for 24 hours.

The resultant product was quite flexible and life like in appearance and is unaffected by normal variations of temperature, humidity and light.

EXAMPLE 9

A fresh "Privet" rose bloom, with hole in the recepticle, was placed in a glass jar containing one quart of 99.8% isopropyl alcohol at a temperature of 32° F., in which had been dissolved 8 grams of 50% phosphoric acid and 5 grams of Irganox 245 antioxidant.

After being held for 2 days at 32° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:
- 20 parts—Short oil alkyl of Example 8
- 10 parts—methylene diphenyldiisocyanate prepolymer from Urethane Industries Equivalent Weight=250
- trace—dibutyl tin dilaurate
- 20 parts—xylene
- 59 parts—methyl ethyl ketone The bloom was then removed from the solution and placed in dry air and held at a temperature of 130° F. for 2 hours.

The resultant product was quite flexible and tough, and life like in appearance and is unaffected by normal variations of temperature, humidity and light.

EXAMPLE 10

A fresh "Sonia" rose bloom, with hole in the recepticle, was placed in a glass jar containing one quart of 99.8% isopropyl alcohol at a temperature of 28° F., in which had been dissolved 8 grams of 50% phosphoric acid.

After being held for 3 days at 32° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:
- 20 parts—Short oil alkyl of Example 8
- 10 parts—Resimene 2040
- traced—ibutyl tin dilaurate
- 70 parts—(methyl ethyl ketone 70% - isopropyl alcohol 30%)

The bloom was then removed from the solution and placed in dry air and held at a temperature of 130° F. for 2 hours.

The resultant product was rigid and shiny, and is unaffected by normal variations of temperature, humidity and light.

EXAMPLE 11

A fresh "Vanda" orchid bloom, with hole in the recepticle, was placed in a glass jar containing 25 ounces of anhydeous tertiary butyl alcohol and 7 ounces of isopropyl alcohol at a temperature of 40° F.

After being held for 3 days at 40° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:

20 parts—Max Polyol E-351 (an ethylene oxide capped poly propylene glycol ether, mo. wt. capped 1000, Union Carbide)
8 parts—hydrogenated methylene diphenyl diisocyanate
trace—dibutyl tin dilaurate
72 parts—methyl ethyl ketone The bloom was then removed from the solution and placed in dry air and held at a temperature of 165° F. for 24 hours.

The resultant product was somewhat rigid, good color and life like in appearance and is unaffected by normal variations of temperature, humidity and light.

EXAMPLE 12

A fresh "Janquil" bloom, with hole in the receptical, was placed in a glass jar containing one quart of 99.8% isopropyl alcohol at a temperature of 32° F., in which had been dissolved 5 grams of Irganox 245 antioxidant.

After being held for 2 days at 32° F. in this sealed container, the bloom was removed, excess solvent was removed from it by briefly blowing dry nitrogen gas on it, and it was then quickly placed in a one gallon polyethylene bucket that had one inch of granulated dessicating clay on its floor. The bucket was then sparged with dry nitrogen gas for 30 seconds and a flat methacrylate sheet (⅛" thick) was placed over the opening.

After 24 hours the dried bloom was removed and dipped in a solution containing:
2 parts—methylene diphenyldiisocyanate
trace—dibutyl tin dilaurate
98 parts—methyl ethyl ketone The bloom was then removed from the solution and placed in dry air and held at a temperature of 80° F. for 36 hours.

The resultant product looks and feels like colored paper, was somewhat rigid, and is unaffected by normal variations of temperature, humidity and light.

EXAMPLE 13

A dehydrated bloom is dipped in a solution of 100 parts of Desmolac 4125 very low hydroxyl content Polyurethane lacquer that has been let down with MEK?Toluen/TBA to 10% solids and to which has been added approximately 1 part of MDI. The bloom is then rid of excess solution and held in a dry atmosphere at 100° F. for one day. Then conditioned for 10 days under normal conditions. The resultant bloom is tough, but somewhat brittle and rather dull in appearance.

Combining Solvent Dehydration and Cross Linking Without First De-wetting the Substrate Under certain circumstances, flower blooms can be cross linked without first removing the solvent that has removed most of the in vivo water. The critical factor is that the solvent itself must be water miscible at the concentration it is used and must not be reactive with the cross linking agent which is required to react with the active hydrogen atoms in the substrate.

Tertiary alcohols such as tertiary butyl alcohol and tert amyl alcohol are suitable, as is diacetone alcohol (mixed tert alcohol and ketone in one molecule). Such things as acetone, methyl ethyl ketone, ethyl acetate, diethyl ether, diisopropyl ether, tetra hydro furan, dioxane and dimethyl formamide are also suitable. The choices are so numerous as to defy a definitive list. It is important to remember that one should choose a solvent that will not react with the bloom, or the cross linking agent, or extract color from it, or cause it to become misshaped, and is rather volatile and inexpensive.

I. When cross linking flowers (and other substrates) in the solvent wet stage, there are several points to remember.

A. When cross linking solvent wetted substrates with aminoplasts (UF/MF), a relatively large amount of water and organic primary and/or secondary hydroxyls in the solvents can be tolerated since they will be driven off by heat curing, as is usual in this type of cross linking reaction. Water content must, however, still be below azeotropic levels.

B. When cross linking solvent wetted substrates with isocyanates, care must be taken to eliminate or avoid introducing water into the system, as well as any organic that maybe present in the solvent. It is quite acceptable to have large quantities of organic tertiary hydroxyls present during the cross linking because they are non-reactive with aromatic isocyanates. Water azeotroping solvents not have to be used in this embodiment.

EXAMPLE 14

A privet rose bloom that has been partially dehydrated to about 2% water in an isopropyl alcohol dehydrating solution is removed from the dehydrating solution, drained and briefly dried with a dry nitrogen gas jet and then immersed in 50% Resimene 970 resin dissolved in an IPA/MEK mixture containing $H_2SO_4$ catalyst. After a residence time of several minutes to hours the bloom is removed, briefly drained, and then dried briefly with a dry nitrogen gas jet and placed in a controlled atmosphere oven that is electrically heated to 140 degrees F. rising to 180 degrees F. for one to six hours, that is vented in a way that allows alcohol/water vapors to escape but no air to enter. The result is a bloom that is cross linked with the appearance and properties of finely formed colored paper. The bloom is dimensionally and color stable but not as strong and durable as blooms cross linked after they have been rid of all water and solvent.

EXAMPLE

Same as Example 14 above except a small amount of styrene/allyl alcohol copolymer resin dissolved in MEK/IPA mixture is added to the Resimene 970 impregnating solution.

The resulting bloom is much more rigid than the previous example and quite frangible.

EXAMPLE 16

A privet rose bloom that was essentially completely dehydrated by immersion in two serial solutions of anhydrous tertiary butyl alcohol is removed and briefly drained and then immersed in a MEK/TBA mixture containing MDI prepolymer and dibutyl tin dilaurate catalyst for several minutes and again drained, then briefly nitrogen gas jet dried, and finally placed in a dry oven maintained at a temperature of 130 degrees F. for up to one hour.

The result is a bloom that is quite similar to finely formed colored paper in appearance and properties and retains both shape and color indefinitely, but it is less durable than a bloom crosslinked after it has been thoroughly dried.

SOLVENT DEHYDRATION AND SOLUTION EVAPORATION

Any conventional drying procedures can be used, such as sand and borax mixtures, silica gel, and mixtures of silica gel with sand and/or borax, activated clays, whether the substrate is surrounded by the drying agent or just in close proximity. Drying agents such as calcium sulfate and its hemi-hydrate, and concentrated sulfuric acid, etc., are also included, as is vacuum freeze drying. All substrates dry by these methods may be subsequently cross linked through active hydrogen sites.

Substrates may be solvent dehydrated by immersion in selected solvents, which are then evaporated. A very large number of permutations and combinations of treating procedures are possible, many of which are described in the prior art, therefore, it is necessary to dwell here only on those aspects of the dehydrating procedures which are novel.

And finally, in the case of substrates that have large masses that are mostly water, it is beneficial to drill holes in said masses before immersion, to facilitate diffusion of the solvent and water. For instance, it is beneficial to drill one or several, holes in the part of the bloom known as the Receptacle. The hole or holes should be about the size of a large pin head and should reach upward into the area that is rich in water and sieves at the base of the Pistols and Stamens. Punching or piercing will also work in these operations, but not as well as drilling.

Having fully described the invention, it is intended that it be limied only by the lawful scope of the appended claims.

I claim:

1. The process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, said substrate including naturally occurring active hydrogen compounds as part of its structure, exposing the substantially dried substrate to a polyisocyanate crosslinking compound containing a plurality of isocyanate groups which are complementary reactive with the said active hydrogen groups to form a high molecular weight three dimensional cross-linked polymeric network between the active hydrogen groups of said substrate and the polyisocyanate compound.

2. The substrate produced by the process of claim 1.

3. The process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, said substrate including naturally occurring active hydrogen compounds as part of its structure, exposing the substantially dried substrate to a aminoplast resin crosslinking compound which is complementary reactive with the said active hydrogen groups to form a high molecular weight three dimensional cross-linked polymeric network between the active hydrogen groups of said substrate and the aminoplast resin compound.

4. The substrate produced by the process of claim 3.

5. The process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, said substrate including naturally occurring active hydrogen compounds as part of its structure, exposing the substantially dried substrate to a polyaldehyde cross-linking compound containing a plurality of aldehyde groups which are complementary reactive with the said active hydrogen groups to form a high molecular weight three dimensional cross-linked polymeric network between the active hydrogen groups of said substrate and the polyaldehyde compound.

6. The substrate produced by the process of claim 5.

7. The process of claim 1, 2 or 5 wherein additional active hydrogen compounds are added to the substrate and react with said cross-linking compound.

8. The process of claim 1, 2 or 5 wherein additional active hydrogen compounds in the form of polyols are added to the substrate and react with said cross-linking compound.

9. The substrate produced by the process of claim 7.

10. The substrate produced by the process of claim 8.

11. The process of claim 1, 2 or 5 wherein the substrate has one or more holes in it prior to dehydration.

12. The process of claim 11 wherein the substrate has a bloom and the holes are in the receptacle of the bloom.

13. The process of claim 12 wherein the holes reach into the sieves at the base of the pistols and stamens, and other holes reach the bases of the sepals and still other holes reach the pedicel.

14. The substrate produced by the process of claim 11.

15. The substrate produced by the process of claim 12.

16. The substrate produced by the process of claim 13.

* * * * *